United States Patent [19]
Aussieker

[11] 3,957,440
[45] May 18, 1976

[54] APPARATUS FOR TESTING CORROSION RESISTANCE OF WORKPIECE SURFACES

[75] Inventor: Klaus Aussieker, Munchenstein, Switzerland

[73] Assignee: Rudolf Wechsler, Birsfelden, Switzerland

[22] Filed: June 27, 1975

[21] Appl. No.: 590,856

[30] Foreign Application Priority Data
June 28, 1974 Switzerland.......................... 8947/74

[52] U.S. Cl............................... 23/253 C; 73/86
[51] Int. Cl.² ................. G01N 17/00; G01N 33/20
[58] Field of Search............ 23/253 C, 230 C; 73/86

[56] References Cited
UNITED STATES PATENTS

| | | | |
|---|---|---|---|
| 3,014,788 | 12/1961 | Littler et al....................... | 23/230 C |
| 3,197,698 | 7/1965 | Schaschl et al................... | 73/86 UX |
| 3,582,282 | 6/1971 | Kampf et al. .................. | 23/253 C X |
| 3,846,795 | 11/1974 | Jones ............................. | 23/253 C X |

Primary Examiner—Robert M. Reese
Attorney, Agent, or Firm—Karl F. Ross; Herbert Dubno

[57] ABSTRACT

An upright cylindrical vessel is formed with a plurality of fittings at its upper end to receive a thermometer, a stirrer, a reflux condenser, means for evacuating or pressurizing the vessel or the like, and is open at its other end which is provided with a circular bead. A pair of clamping rings, one of which engages behind the bead, are bridged by clamping screws to secure a disk of the workpiece material to the open end of the vessel. The corrosive medium is introduced into the vessel and attacks the workpiece surface exposed therein.

14 Claims, 1 Drawing Figure

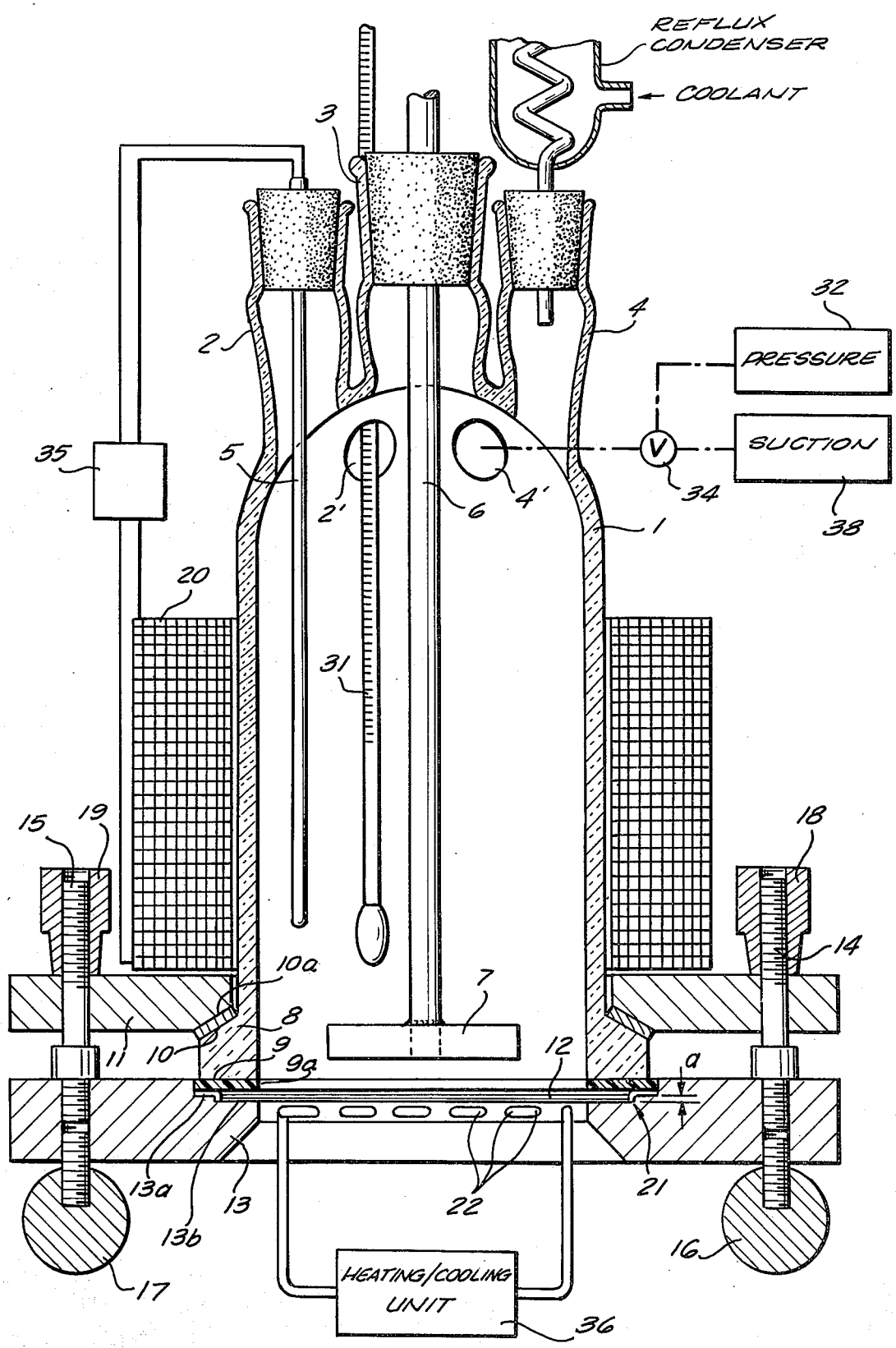

APPARATUS FOR TESTING CORROSION RESISTANCE OF WORKPIECE SURFACES

FIELD OF THE INVENTION

The present invention relates to an apparatus for testing specimens of different workpiece materials, in the form of disks, for resistance to corrosive media, e.g. acids, bases and other liquids which may be processed in reactors or the like made from the workpiece.

BACKGROUND OF THE INVENTION

In the testing of materials for use as container walls, reactors in chemical and allied industries and elsewhere using corrosive media, it has been proposed to provide various apparatuses which are intended to render the tests as reproducible as possible.

For example, a test apparatus for the testing of the resistance of enamels to boiling liquids is described in GERMAN INDUSTRIAL STANDARD (DIN) 51157 and comprises a glass cylinder in whose cylindrical wall two fittings are provided for the connection of a reflux condenser and for mounting a thermometer. At both of the ends test specimens can be mounted, with interposition of seals, between triangular plates.

This apparatus has the disadvantage that it does not allow for the stirring or agitation of the corrosive media. A further disadvantage is that with long use sealing problems ensue.

The inability to provide for an extensive agitation of the corrosive medium is a serious disadvantage since only by extensive stirring can a uniform temperature distribution be ensured and it is possible to most effectively use a temperature control device or even do without one if such use is desired.

Furthermore, with the above-mentioned prior device, it is not possible to provide the temperature-sensitive devices, e.g. thermometer, directly in the heated zone of the liquid medium and hence the thermometer is confined only to the vapor space above the medium. Consequently, it is not possible to accurately know the temperature of the medium at the active interface between the corrosive medium and the workpiece specimen.

OBJECT OF THE INVENTION

It is the principal object of the present invention to provide an improved apparatus for the testing of the corrosion resistance of workpiece specimens.

Still another object of the invention is to provide an apparatus for the purposes described which is free from the above-mentioned disadvantages and allows especially reproducible results for long periods without leakage difficulties.

SUMMARY OF THE INVENTION

The above and other objects are attained, in accordance with the present invention, in an apparatus for testing the resistance of a workpiece surface, especially in the form of a flat specimen disk, to a corrosive flowable medium, which comprises a vessel of a material resistant to corrosion by said medium, preferably glass, having an opening at one end and an annular external bead surrounding this opening.

A pair of clamping members receiving the workpiece between them can be drawn together by a tightening means to retain the workpiece disk against the end of the vessel, one of the clamping members surrounding the vessel and engaging behind the bead.

Advantageously, the vessel is circularly cylindrical, at least at the opening, and the opening is coaxial with the right circular cylinder. The bead then, of course, is circular and preferably has a frustoconical ground surface constituting an external shoulder which is engaged by a complementary surface of a recess of countersunk in the bore of the clamping ring constituting the above-mentioned one of the clamping members.

The tightening means preferably is constituted by a plurality of bolts interconnecting the clamping rings and each including a threaded element tightenable to draw the rings together. The other clamping ring or member has a bore aligned with the opening and is formed, on its side facing the vessel, with a step concentric with the bore and receiving the workpiece disk. A sealing ring is received in the step between the open end of the vessel and the workpiece.

Advantageously, the step has an inner portion of an axial height smaller than the thickness of the workpiece disk so that the sealing ring will bear only between the vessel and the workpiece and will not engage a shoulder of the clamping ring. The vessel is formed with at least one fitting, but preferably a plurality of fittings, to allow various elements of the apparatus to be connected thereto.

For example, one fitting may be reserved for a reflux condenser, a vacuum pump for evacuating the vessel or a source of a pressurizing gas. A central fitting, coaxial with the vessel and the opening, can receive the rod of a stirrer whose blades lie proximal to the workpiece surface exposed to the interior of the vessel. One or more further fittings can be provided to receive an indicatng a thermometer and/or a resistance thermometer adapted to control an annular heating element which can surround the vessel adjacent the disk.

The clamping ring or member remote from the vessel can be formed with a bore in which a coil of tubing is disposed adjacent to the surface of the workpiece turned away from the vessel, this coil being connected to a source of heating and/or cooling fluid to enable variation of the temperature of the workpiece from the exterior of the system.

The provision of an annular bead to secure the test disk to the vessel via the clamping members, especially by sandwiching the test disk between the clamping members and against the vessel, greatly facilitates mounting without any danger of leakage, especially where a replaceable seal is provided between the workpiece and the open end of the vessel.

The apparatus has a number of significant advantages:

The temperature of the liquid medium and its vapors can be determined at any level in the vessel and consequently, control as desired. A precise establishment of the test temperature corresponding to the temperature at which the workpiece will operate with the corrosive medium is possible.

All of the portions of the apparatus which come into contact with the corrosive medium can be composed of glass (a preferred material for the vessel) or like corrosion resistant substances. The effect on the corrosive process by traces of metal from the testing apparatus itself can be excluded.

All of the fittings can be provided with conventional ground joints to enable the apparatus to be especially gas-tight, and, where desired, vacuum tight.

The clamping technique greatly simplifies the sealing and mounting of the test specimen at the bottom of the glass cylinder.

The apparatus allows the testing of a variety of workpieces with substantially any corrosive medium for prolonged periods without difficulty and, with a high degree of reproducibility.

Since the sealing of the vessel against the workpiece takes place inwardly of the periphery of the workpiece disk, there is no attack upon the edges of the workpiece which is especially of importance in the testing of synthetic-resins and material coated therewith. A true test of the coating can thus be obtained.

The test can reproduce the agitation which is to take place in the reactor for which the test material is contemplated so that the erosion effects in the presence of suspensions or solid particles, can be tested simultaneously.

In this application, reference is made to a flowable medium and it should be noted that this is intended to include pure liquids as well as emulsions, suspensions, dispersions, colloidal suspensions, oleogenic substances, deposits and the like. The term, however, also contemplates fine powders and solid materials which flow like liquid.

BRIEF DESCRIPTION OF THE DRAWING

The sole FIGURE of the drawing is a somewhat diagrammatic vertical cross-sectional view of an apparatus embodying the present invention.

SPECIFIC DESCRIPTION

In the drawing I show a substantially circularly cylindrical (right circular cylinder) glass vessel 1 which may be composed of chemical apparatus glass such as DURAN 50, having a spherically domed upper portion provided with a main fitting 3 and two auxiliary fittings 2 and 4 although openings for other fittings have been shown at 2' and 4', these latters fittings being behind the fittings illustrated.

The main fitting 3 is formed with a conventional ground glass joint and is axially aligned with the bottom or open end of the vessel and receives the shaft 6 of a KPG stirrer with a conventional KPG seal serving as the bearing. At its lower end that shaft carries stirrer blades 7 which are welded (permanently fixed to the shaft) or screwed to the shaft (removable therefrom). A screw connection has been found to be especially advantageous since it permits replacement of the blades to achieve different stirring effects.

Externally of the vessel 1 and above the latter but not seen in the drawing, is a conventional drive arrangement for this shaft.

A glass resistance or noise thermometer Pt100, with a conventional ground glass joint, is received in the conventional ground glass joint of fitting 2.

The fitting 4, likewise with a ground glass joint, receives the reflux condenser which can be cooled with circulated or noncirculated water or the like.

A further fitting 2' can receive, via conventional ground glass joints, an indicator thermometer 31 while the fitting 4' can be connected by ground glass joints with a pressure source 32 or a suction source 33 as determined by the setting of a valve 34. The latter means serves for evacuation, degassing, pressurization or the like. The pressure means can feed a predetermined quantity of the corrosion medium into the system.

At the bottom of the vessel, the latter is formed with a radially outward extending bead or flat 8 of trapazoidal cross-section with a frustoconical ground surface engaged by a clamping member or ring 11. The end of the vessel is a flat ground angular surface 9.

The clamping members 11 and 13 are composed of stainless and acid-resistance steel. The lower ring 13 is formed with a step accommodating the test disk 12 and a seal 9a and is designed to center the specimen relative to the glass vessel 1. Surrounding the step is a multiplicity of upwardly extending threaded pins or screws 14, 15, angularly equispaced about the axis of the apparatus and engaged by hexagonal nuts 18, 19 which draw the clamping members together.

The ring 11 is provided with a bore allowing it to be placed over the vessel 1, the bore being countersunk to form a frustoconical recess complementary to the frusto cone of bead 8. Between this recess and the bead, an elastic (rubber) ring 10a can be introduced to cushion the engagement of the ring 11 with the surface 10 of bead 8.

The seal 9a can be composed of a corrosion resistant material such as polytetrafluroethylene (Teflon).

An annular heater 20 operated by a temperature controller 35 and the resistance thermometer 5 surrounds the glass vessel 1.

In operation, a test disk 12 is formed from the material whose corrosion resistance is to be determined and is inserted on a seat 13b in the step end portion of the ring 13, the shoulder 13a of the step portion being located at a height less than the thickness of the test specimen. The Teflon seal 9a is then placed upon the specimen 12 and the end 9 of the vessel 1 is mounted so that it lies inwardly of the periphery of the step. The ring 11 is then clamped to the ring 13 and the heating coil 20 can be mounted upon the unit.

The heating coil is controlled electronically at 35, e.g. by a SYSTAG-TCU 2, and the corrosion medium is introduced. The thermometer 5 can be positioned either in the liquid or in the vapor phase as required and the appropriate temperature is applied together with stirring or any pressure or vacuum as may be desired.

The reflux condenser recycles vapor to the system. The peripheral edge of the workpiece designated at 21 does not encounter the corrosion media and coils 22 of tubing can be supplied with heating or cooling fluid from the unit 36 to regulate the temperature of the workpiece.

The apparatus can be operated with domed specimens as well, as long as the peripheral edge of the specimen is planar. Of course the pyre spiral 22 can be replaced by an electric heating spiral if desired. Feet 16 and 17 can be applied to support the apparatus. The vessel 1 can also be made of stainless steel or other corrosion resistant materials, if desired, the test disk 12 can be backed up by a supporting steel disk.

I claim:

1. An apparatus for testing the resistance of a workpiece surface to a corrosive flowable medium, especially a liquid, said apparatus comprising:

a vessel of a material resistant to corrosion by said medium and adapted to receive said medium, said vessel being formed with an opening and an annular external bead surrounding said opening;

a pair of clamping members receiving said workpiece between them, one of said members annularly engaging said bead; and releasable tightening means for drawing said members together, thereby retaining said workpiece across said opening and securing said workpiece to said vessel.

2. The apparatus defined in claim 1 wherein said vessel is upright generally circular cylinder at least at said opening and said opening is centered in said vessel, said bead being circular, said clamping members are formed as respective rings, and said tightening means includes a plurality of bolts interconnecting said rings and each including a threaded element tightenable to draw said rings together.

3. The apparatus defined in claim 2 wherein the other of said members is formed with a bore and a step concentric with said bore, said step receiving said workpiece and said apparatus further comprising a sealing ring received in said step between said vessel and said workpiece.

4. The apparatus defined in claim 3 wherein said step has an inner recess portion adapted to receive said workpiece and having an axial height smaller than the thickness of the workpiece whereby said sealing ring bears only against said workpiece and said vessel.

5. The apparatus defined in claim 4 wherein said vessel is formed with at least one fitting communicating with the interior thereof.

6. The apparatus defined in claim 5, further comprising a vacuum source connected to said fitting for evacuating said vessel.

7. The apparatus defined in claim 5, further comprising a pressure source connected to said fitting for pressurizing said vessel.

8. The apparatus defined in claim 5 wherein said fitting is substantially coaxial with said opening, said apparatus further comprising a stirrer mounted in said vessel and including a shaft extending through said fitting toward said opening, and blade means on said shaft proximal to said opening.

9. The apparatus defined in claim 5 further comprising an annular heater surrounding said vessel over at least a portion of the length thereof.

10. The apparatus defined in claim 9 further comprising a resistance thermometer responsive to the temperature in said vessel.

11. The apparatus defined in claim 5 further comprising temperature control means adjacent said workpiece and externally of said vessel for varying the temperature thereof.

12. The apparatus defined in claim 11 wherein said temperature control means is a heater.

13. The apparatus defined in claim 11 wherein said temperature control means is a cooler.

14. The apparatus defined in claim 11 wherein said temperature control means includes a tubing coil within said bore of said other member, and a source of a temperature-control fluid connected to said coil.

* * * * *